United States Patent [19]

Hilverda

[11] Patent Number: Plant 7,115

[45] Date of Patent: Jan. 16, 1990

[54] CARNATION NAMED HILBIRD

[75] Inventor: Jan J. Hilverda, Aalsmeer, Netherlands

[73] Assignee: Hilverda b.v., Aalsmeer, Netherlands

[21] Appl. No.: 308,752

[22] Filed: Feb. 10, 1989

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new spray carnation variety particularly characterized by its continuous blooming habit with profuse production of relatively small flowers having a moderate number of imbricated petals with an overall lavender lilac coloration, the flowers being borne on erect, rigid stems of about 60 cm. in length emitted from a plant having a strong, vigorous and upright growth habit with abundant foliage and a total height averaging about 110 cm.

1 Drawing Sheet

BACKGROUND OF THE NEW PLANT

This new spray carnation cultivar originated as a seedling of a hybrid resulting from my crossing of two unnamed and unpatented carnation varieties selected from my collection of carnation plants maintained by me for breeding purposes at Aalsmeer, The Netherlands, the object of this crossing being to improve the range of varieties for commercial production by having more rapid growth, better flower colors and improved production rate. This particular seedling was selected by me because of the lovely overall lavender lilac coloration of its small but dainty flowers and propagation of this new plant was done by me at Aalsmeer by means of cuttings with very satisfactory results. For that reason, this new carnation variety was propagated under my direction at Aalsmeer for several successive generations by means of cuttings, which demonstrated conclusively that the distinctive characteristics of the original seedling would be maintained from generation to generation and appeared to be firmly fixed.

DESCRIPTION OF THE DRAWING

This new spray carnation cultivar is illustrated by the accompanying photographic drawing which shows, in full color, a flowering stem having blooms and buds in several stages of maturity, as well as a full face view of the flower, several petals and a bud about to reach its opening stage, the colors shown being as nearly true as it is reasonably possible to obtain by conventional photographic procedures.

DESCRIPTION OF THE NEW PLANT

The following is a detailed description of my new spray carnation variety based upon observations made during the current year at Aalsmeer, the color designations being according to The R.H.S. Colour Chart and The Robert F. Wilson Horticultural Colour Chart (H.C.C.), both issued by The Royal Horticultural Society of London, England.

THE PLANT

Origin: Seedling.

Parentage:

*Seed parent.*—An unnamed and unpatented variety.

*Pollen parent.*—An unnamed and unpatented variety. Both varieties having been selected by me from my collection of carnation varieties maintained by me at my nursery in Aalsmeer for breeding purposes.

Classification:

*Botanic.*—*Dianthus caryophyllus* L.

*Commercial.*—Spray Carnation.

Form: An erect and tall bush.

Growth: Vigorous and upright with good strength.

Branching character: Alternate.

Foliage:

*Quantity.*—Abundant.

*Size of leaf.*—About 9 to 10 cm.

*Shape.*—Elliptic with entire margins.

*Texture.*—Leathery.

*Color.*—Both upper and under sides: Blue green.

*Leaflets.*—None.

*Ribs and veins.*—The midrib is prominent.

THE BUD

Size: Medium.

*Diameter.*—About 10 to 12 mm.

*Length.*—Approximately 25 mm.

Shape: Cylindrical.

Opening rate: With a mature bud, the flower petals appear in approximately five days.

Color of petals: Lavender lilac when sepals first divide and when the petals begin to unfurl.

Sepals:

*Number.*—Five.

*Shape.*—Long ovate with an acute apex.

*Character.*—The sepals are hooded over the bud before dividing and stand up as the flower petals unfurl.

*Color.*—Inside: Light Green. Outside: Dark Green.

*Striae.*—Very few, small and Light Green/Yellowish in color.

Calyx:

*Shape.*—Cylindrical.

*Size.*—Medium.

*Splitting.*—The calyx does not split.

*Aspect.*—Smooth.

Flower stem:

*Length.*—Averages about 70 cm.

*Character.*—Rigid and erect.

*Color.*—Dark Green.

THE FLOWER

Blooming habit: Continuous with profuse flower production.

Size of bloom: Small.

*Diameter.*—About 40 to 45 mm.

*Depth.*—About 15 to 20 mm.

Borne: In clusters on straight stems emitted in longitudinally-spaced relation from a tall, strong and erect main stem.

Flower shape:

*When bloom first opens.*—A high center.

*When bloom matures.*—It tends to flatten.

Petalage:

*Number of petals.*—Averages about 28 to 32.

*Arrangement.*—Imbricated.

*Form.*—Fan-shaped with serrate-crenate margins and rounded outer end.

*Texture.*—Soft.

*Aspect.*—Velvety.

*Color.*—All petals: Body — Lavender Lilac, H.C.C. 628/2.

Flowering stem:

*Length.*—About 70 cm.

*Character.*—Rigid and erect.

*Color.*—Dark green.

Discoloration after full bloom: None.

Fragrance: Weak but only when flower is mature.

Persistence: The flowers hang on and dry.

Lasting quality: As a cut flower, about ten to fourteen days.

REPRODUCTIVE ORGANS

Stamens:

*Number.*—Five or six.

*Arrangement.*—Evenly around the ovary.

*Anthers.*—Size: Normal. Color: Cream white.

*Filaments.*—Length: About 15 mm. Color: White.

*Pollen.*—Color: White.

Pistils:

*Number.*—One.

*Style.*—Length: From 20 to 25 mm. Color: White.

*Stigmas.*—Color: White.

Character of ovaries: Normal.

THE FRUIT

Fertility: The fruit is fertile.

Shape: Lozenge-shaped.

Color at maturity: Yellow/Brown.

This carnation variety most nearly resembles the variety 'Tony' (unpatented) but is distinguished from 'Tony' by a totally different color, a darker leaf color and a more rapid and taller growth habit.

I claim:

1. The new and distinct spray carnation variety, substantially as herein shown and described, characterized by its relatively small flowers having an overall lavender-lilac coloration, its profuse production of blooms carried on a long flower stem, and its vigorous and upright growth habit with abundant foliage.

* * * * *

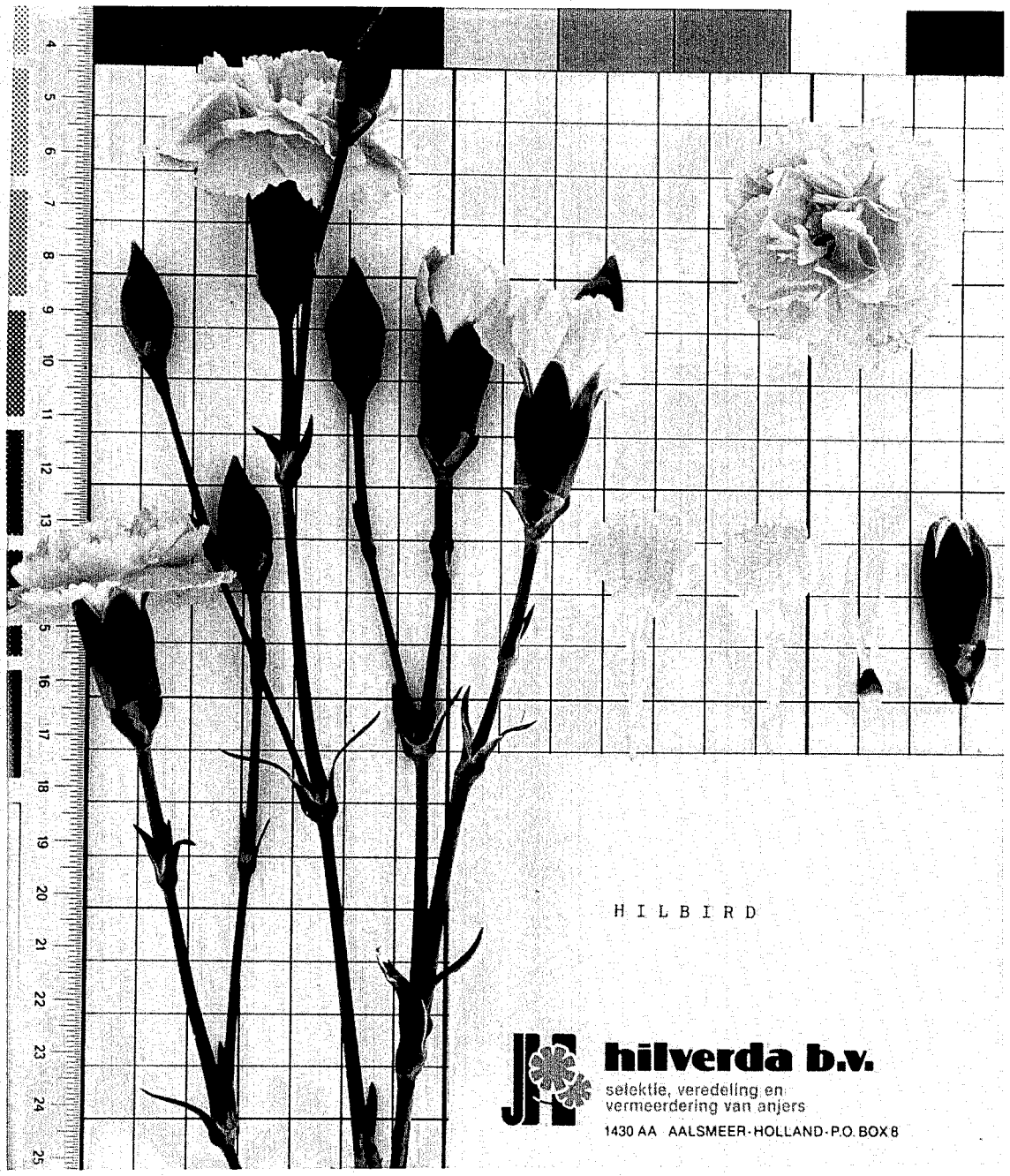
HILBIRD
hilverda b.v.
selektie, veredeling en
vermeerdering van anjers
1430 AA AALSMEER-HOLLAND-P.O. BOX 8